United States Patent [19]

Sotoya et al.

[11] Patent Number: 4,705,893

[45] Date of Patent: Nov. 10, 1987

[54] PROCESS FOR THE PREPARATION OF AMPHOTERIC SURFACTANTS

[75] Inventors: Koshiro Sotoya; Makoto Kubo; Kazuhiko Okabe, all of Wakayama, Japan

[73] Assignee: Kao Corporation, Tokyo, Japan

[21] Appl. No.: 931,372

[22] Filed: Nov. 14, 1986

[30] Foreign Application Priority Data

Nov. 25, 1985 [JP] Japan ................................. 60-264492

[51] Int. Cl.$^4$ ......................................... C07C 103/183
[52] U.S. Cl. ..................................... 562/564; 548/354
[58] Field of Search ......................... 562/564; 548/354

[56] References Cited

U.S. PATENT DOCUMENTS 4,020,155  4/1977  Kalopissis et al. .............. 562/564 X

OTHER PUBLICATIONS

Derwent Abstract of Japan Kokai 61-143347, 7/1/86.

*Primary Examiner*—Richard A. Schwartz
*Attorney, Agent, or Firm*—Flynn, Thiel, Boutell & Tanis

[57] ABSTRACT

An imidazoline compound, suitable for an amphoteric surfactant, is prepared from by reacting (a) an alkylimidazoline with a monohaloacetic acid in (b) a lower alcohol and (c) water in the presence of an alkali, by-production of inorganic salts being prevented by controlling proportions of (a), (b) and (c) within the scope shown in the drawing.

3 Claims, 1 Drawing Figure

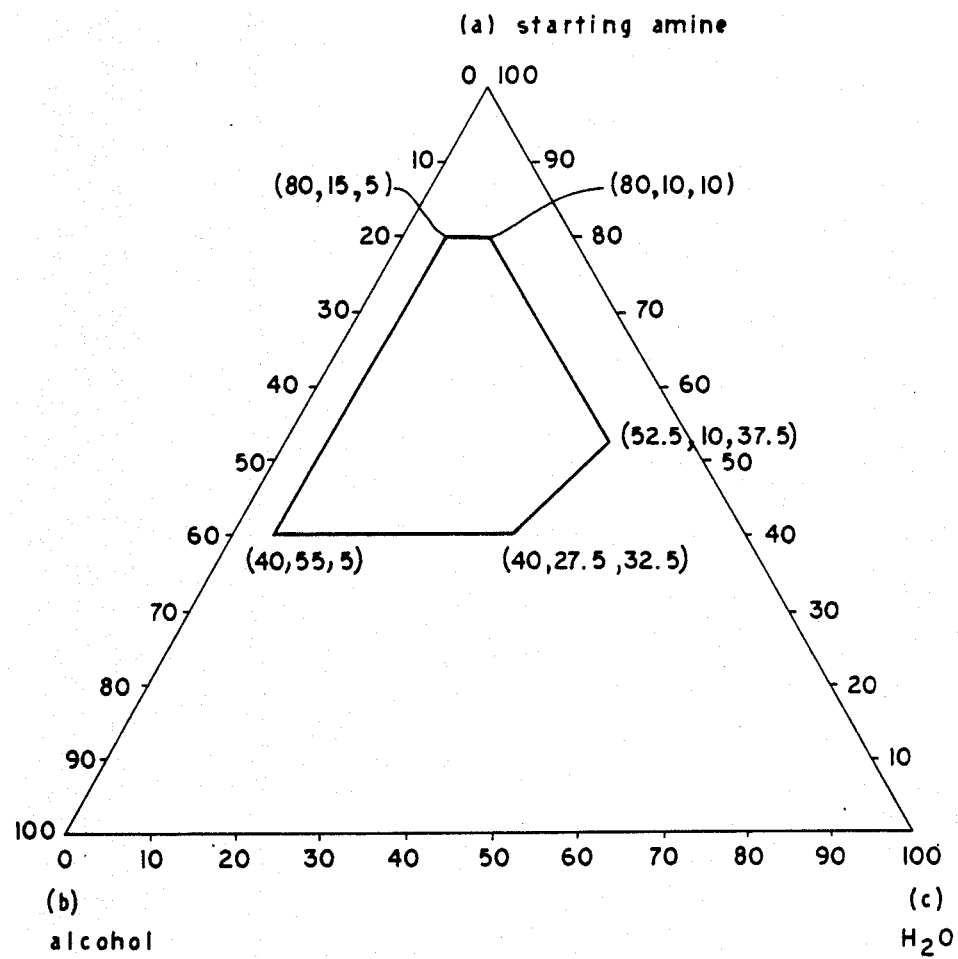

PROCESS FOR THE PREPARATION OF AMPHOTERIC SURFACTANTS

The present invention relates to a process for the preparation of an amphoteric surfactant, more particularly, to a process for the preparation of an imidazoline amphoteric surfactant having a low inorganic salt content.

STATEMENT OF PRIOR ART

Recently, imidazoline amphoteric surfactants have widely been used as the base for shampoo, detergent or the like to cope with an enhancing demand for safety or low stimulus, because they are lowly stimulant to the skin or the eyes. An imidazoline amphoteric surfactant is generally prepared by converting an alkylimidazoline into an amphoteric compound by reacting it with a monochloroacetic acid or its sodium salt. Further, with respect to the imidazoline amphoteric surfactant thus prepared, it has been found as the result of recent studies that it hardly contains an imidazoline skeleton which the above surfactant has long been believed to have, but comprises amidamine derivatives obtained by a ring-opening reaction of imidazoline. Examples of the amidamine derivative prepared by the above reaction include compounds represented by the following formula:

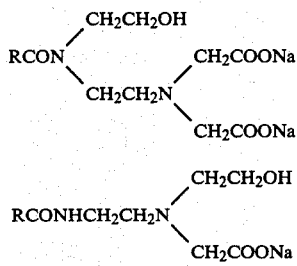

However, the surfactant prepared by the above reaction is generally called "imidazoline surfactant" by usage. Therefore it will be similarly called in this specification.

As described above, such an imidazoline amphoteric surfactant can be prepared by reacting an imidazoline or its hydrolyzate, i.e., amidamine, with monochloroacetic acid or its sodium salt. In this process, an alkali (for example, an aqueous NaOH solution) must be used to neutralize a generated acid, thus enhancing the yield. Accordingly, the obtained imidazoline surfactant contains a large amount of an inorganic salt (for example, NaCl) formed as a by-product. As a result it has the following disadvantages:

(1) increase in the viscosity of a product, (2) lowering of the low-temperature stability of a product containing such a surfactant, and (3) difficulty in compounding it with other surfactants (demulsification).

Particularly, the disadvantage(1) of an increase in the viscocity of a product due to a by-product inorganic salt significantly limits the composition of a product. Thus, an imidazoline surfactant of a glycine type derived from monochloroacetic acid contains an active ingredient only in a low concentration of 30 to 40 %, so that it has a large demerit in aspects of production efficiency, limitation in compounding and the like.

Accordingly, if it be possible to reduce the amount of an inorganic salt formed as a by-product which is present in an imidazoline amphoteric surfactant of a glycine type, a large merit will be brought about in aspects of productivity and uses. Although the desalting of such an imidazoline amphoteric surfactant can be carried out by the use of an ion exchange resin on a laboratory scale, this desalting process is industrially disadvantageous because of its complicated operation and its high cost. Further, although the desalting can be also carried out by the use of an extraction solvent (see Japanese patent Laid-Open No. 75998/1984), this process requires the removal and recovery of the extraction solvent, thus being disadvantageous in an aspect of cost.

BRIEF DESCRIPTION OF THE DRAWING

FIG. 1 is a graph showing the reaction condition characteristic of the present invention.

SUMMARY OF THE INVENTION

With the purpose of solving the above problem, the inventors of the present invention have studied on a process for the preparation of an imidazoline amphoteric surfactant which can be efficiently carried out on an industrial scale and wherein the desalting can be carried out by simple operation and have accomplished the present invention.

The present invention provides a process for the preparation of an amphoteric surfactant comprising reacting an alkylimidazoline or an open-ring derivative thereof with a monohaloacetic acid or a salt thereof in the presence of an alkali in a water/lower alcohol mixture, characterized by carrying out the reaction by using (a) an alkylimidazoline or an open-ring derivative thereof, (b) a lower alcohol and (c) water each in such an amount that the composition by weight of the components (a), (b) and (c) is within a pentagon defined by points (80,10,10), (80,15,5), (40,55,5) (40, 27.5, 32.5) and (52.5,10,37.5) in triangular coordinates wherein each of the components (a), (b) and (c) is placed at each the three vertices of the coordinates and removing precipitated inorganic salts by filtration. FIG. 1 shows the above pentagon. If the content of the water (c) is less than 5%, the reactivity will not be sufficient, while if the content of the lower alcohol (b) is less than 10%, gelation will occur unfavorably.

The alkylimidazoline to be used in the present invention is represented by the general formula (1), while the open-ring derivative thereof is represented by the general formula (2) and (3):

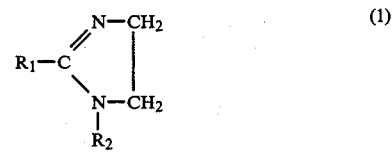

wherein $R_1$ stands for an alkyl or alkenyl group having 7 to 21 carbon atoms and $R_2$ stands for a hydrogen atom or a hydroxyalkyl group having 2 to 4 carbon atoms,

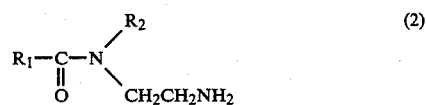

wherein $R_1$ and $R_2$ are as defined above with respect to the general formula (1),

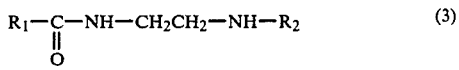

wherein $R_1$ and $R_2$ are as defined above with respect to the general formula (1).

In calculating the weight ratio of an alkylimidazoline or an open-ring derivative thereof used as the component (a), the weight of the open-ring derivative must be calculated in terms of the corresponding cyclic alkylimidazoline itself.

When using the open-ring derivative the weight ratio of the water (c) can be calculated by using the amount of water used as such, while when using the cyclic alkylimidazoline itself, the weight ratio of the water (c) must be calculated by using the amount of water excluding the one required for the ring opening of the alkylimidazoline (1 mol of water per mol of an alkylimidazoline).

Examples of the lower alcohol (b) include alcohols having 1 to 3 carbon atoms, among which ethyl alcohol and isopropanol are preferred. Water may be fed either at the beginning of the reaction or during the reaction or in the form of an aqueous solution of an alkali.

The reaction between an alkylimidazoline or an open-ring derivative thereof (hereinafter sometimes referred to as "feed amine") and a monochloroacetate can be carried out in a water/lower alcohol mixture according to an ordinary method. To explain in more detail, a feed amine is reacted with a monohaloacetic acid or a salt thereof in a water/lower alcohol mixture at 50° to 90° C. under stirring and an alkali is dropwise added to the reaction mixture so as to maintain the mixture at a pH of 8 to 12, or alternatively, a feed amine and a monohaloacetate are fed together with an alkali salt such as $NaCO_3$ or $NaHCO_3$ and the mixture was stirred at 50° to 90° C. to carry out the reaction.

After the completion of the reaction, the reaction mixture is filtered preferably under heating to remove precipitated salts, thus obtaining an imidazoline surfactant having a low inorganic salt content.

The preferred reaction temperature is 50° to 90° C. If the reaction temperature is lower than 50° C., a feed amine will be difficultly dissolved to result in a slow reaction, while if it is higher than 90° C., the obtained amphoteric surfactant will be significantly colored, which is not preferred. The reaction may be carried out either under a normal pressure or under an elevated pressure.

Examples of the feed amine to be used in the present invention include 2-heptylimidazoline, 2-undecylimidazoline, 2-heptadecylimidazoline, 1-hydroxyethyl-2-undecylimidazoline, 1-hydroxyethyl-2-heptadecylimidazoline, N-lauroylethylenediamine, N-stearoylethylenediamine, N-lauroyl-N'-2-hydroxyethylethylenediamine and N-stearoyl-N'-2-hydroxyethylethylenediamine. Examples of the monohaloacetic acid or its salt include monochloroacetic acid, monobromoacetic acid, sodium monochloroacetate and potassium monobromoacetate. Examples of the alkali include caustic soda, caustic potash, sodium carbonate, potassium carbonate, sodium hydrogencarbonate and potassium hydrogencarbonate. However, an alkali (e.g. $Mg(OH)_2$ which forms a salt (e.g. $MgCl_2$) highly soluble in a water/solvent mixture is unsuitable for the process of the present invention.

The molar ratio of the monohaloacetic acid or the salt thereof to the feed amine may be at least 1.0. If the molar ratio is less than 1.0, the feed amine will be converted into an amphoteric surfactant only in a low yield, which is not preferred. Therefore, the molar ratio of the monohaloacetic acid or the salt thereof to the feed amine is preferably 1.0 to 3.0. It is generally preferred that the molar amount of the alkali fed is twice that of the monohaloacetic acid fed or equal to that of the monohaloacetate fed.

According to the present invention, a highconcentration imidazolinium amphoteric surfactant containing less than 1.3%, preferably less than 1.0% of an inorganic salt per 10% of an active ingredient can be easily obtained.

To describe the imidazoline amphoteric surfactant of a glycine type prepared according to the present invention in more detail, the surfactant contains at least one compound selected from among the following three compounds:

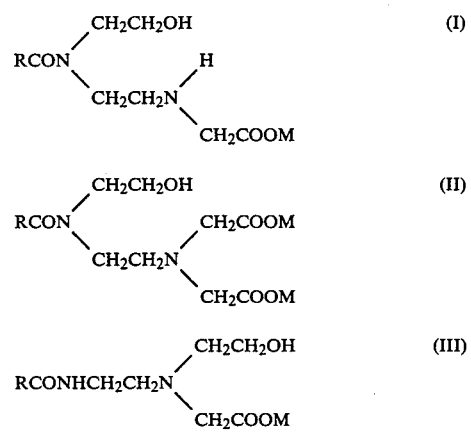

wherein R stands for an alkyl or alkenyl group having 7 to 21 carbon atoms and M stands for a hydrogen atom or an alkali metal.

[Function]

The reason why a high-concentration amphoteric surfactant having a low inorganic salt content can be prepared by the process of the present invention is thought to be as follows: The reaction system of the process of the present invention is kept hydrophobic to a suitable extent by restricting the composition by weight of the components (a), (b) and (c) within a specified range, so that an inorganic salt generated during the reaction can be easily precipitated, and the viscosity of the amphoteric surfactant is lowered by the presence of a lower alcohol. Accordingly, the addition of a lower alcohol after the completion of the reaction is not preferred, not only because the precipitated inorganic salt has too fine a particle size to filter off, but also because gelation occurs in the reaction system.

[EXAMPLE]

The present invention will now be described in more detail by the following Examples.

EXAMPLE 1

268 g of 1-hydroxyethyl-2-undecylimidazoline, 54 g of water and 1.2 g of sodium hydroxide were fed to a 1l four-necked flask fitted with a stirrer, a cooling tube, a dropping funnel and a thermometer. The content was heated to 70° C. under stirring and further stirred for about 4 hours at this temperature to carry out the ring opening. 45.3 g of water, 124 g of ethanol and 233 g of sodium monochloroacetate were fed to the flask and the obtained mixture was aged at 75° to 80° C. for about one hour.

166.7 g of a 48% aqueous solution of NaOH was dropwise added to the obtained solution at the same temperature over a period of about 2 hours and the obtained mixture was further aged at this temperature for 4 hours. Precipitated common salt was filtered off by the use of a pressure filter at 70° C. under a nitrogen pressure of 2 kg/cm². According to the result of liquid chromatographic analysis, 766 g of a solution of N-lauroyl-N'-(2-hydroxyethyl)-N'-sodiumcarboxymethylethylenediamine was obtained. The NaCl content of this solution was confirmed to be 3.9% by analysis thereof for the Cl ion content, and analyses VL (volatile content) and $H_2O$ content revealed that the solution contained 15.2% of ethanol, 23.5% of $H_2O$ and 57.5% of an active ingredient and it was light yellowish brown and viscous at a room temperature and had a 1% pH of 10.3.

EXAMPLE 2

287 g of 1-hydroxyethyl-2-cocoalkylimidazoline, 62 g of water, 233 g of sodium monochloroacetate and 174 g of isopropanol were fed to the same flask as the one used in Example 1 and the content was heated to 70° C. under stirring and aged at this temperature for about one hour. 200 g of a 40% aqueous solution of NaOH was dropwise added to the obtained solution at a constant rate over a period of about 4 hours. The obtained mixture was further aged for 4 hours at that temperature and filtered in a similar manner to the one described in Example 1 to remove precipitated common salt.

According to the result of liquid chromatographic analysis, the reaction product was 801g of a mixture of amphoteric surfactants represented by the following structural formulas:

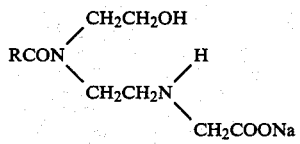

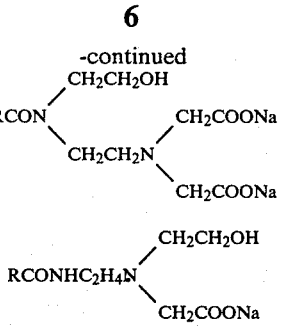

The NaCl content of the solution was confirmed by analysis thereof for Cl ion content to be 2.3%, and the analyses for the VL and $H_2O$ content revealed that the solution contained 20.0% of IPA, 21.7% of $H_2O$ and 56.0% of an active ingredient and it was light brown and liquid at a room temperature and had a 1% pH of 10.5.

EXAMPLE 3

287 g of 1-hydroxyethyl-2-cocoalkylimidazoline, 64 g of water and 1.2 g of NaOH were fed to the same flask as the one used in Example 1 and the content was heated to 80° C. under stirring and further stirred at this temperature for about 4 hours to carry out the ring opening of the imidazoline. 72 g of ethanol and 174.8 g of sodium monochloroacetate were fed to the flask and the mixture was aged at 75° to 80° C. for one hour. 56.7 g of $Na_2CO_3$ was fed to the obtained solution little by little and, after the completion of the feeding, the obtained mixture was aged at the temperature for 4 hours. Precipitated common salt was filtered off in a similar manner to the one described in Example 1 and liquid chromatographic analysis revealed that 511.4 g of a solution of N-cocoyl-N'-(2-hydroxyethyl)N'-sodium-carboxymethylethylenediamine was obtained.

This solution was confirmed by analysis thereof for Cl ion, VL and $H_2O$ contents to contain 1% of NaCl, 13.3% of ethanol and 8.4% of water, and it was in a state of a light brown paste at a room temperature and had a 1% pH of 9.5.

In Examples 4 to 6 and Comparative Examples 1 to 3, 1-hydroxyethyl-2-cocoalkylimidazoline was used as a starting material. The kinds of the alcohols and alkalis used and the compositions of the feeds and the products are listed in the following Table.

It can be understood from the results that the inorganic salt content of an imidazoline amphoteric surfactant can be lowered to 1.3% per 10% of an active ingredient by restricting the composition of the components (a), (b) and (c) within a specified range according to the present invention.

|  |  | Example | | | | | | Comparative Example | | |
|---|---|---|---|---|---|---|---|---|---|---|
|  |  | 1 | 2 | 3 | 4 | 5 | 6 | 1 | 2 | 3 |
| Feed Spec. | feed amine | 47.9 | 45.9 | 70.9 | 48.8 | 61.8 | 47.0 | 34.8 | 42.0 | 29.1 |
|  | solvent* | EtOH | IPA | EtOH | IPA | EtOH | EtOH | EtOH | EtOH | EtOH |
|  |  | 22.1 | 27.8 | 17.8 | 40.1 | 21.1 | 21.3 | 14.0 | 18.3 | 41.8 |
|  | $H_2O$ | 30.0 | 26.2 | 11.4 | 11.0 | 17.1 | 31.7 | 51.1 | 39.7 | 29.1 |
|  | kind of alkali | NaOH | NaOH | $Na_2CO_3$ | $NaHCO_3$ | $Na_2CO_3$ | NaOH | NaOH | NaOH | $Na_2CO_3$ |
| Main component(s) |  | (III) | (I), (II), (III) | (III) | (III) | (III) | (III) | (III) | (III) | (I), (II), (III) |
| Product Analysis | active ingredient | 57.5 | 56.0 | 77.1 | 58.7 | 67.7 | 52.4 | 40.2 | 47.9 | 37.9 |
|  | solvent | 15.2 | 20.0 | 13.3 | 32.8 | 10.5 | 13.7 | 10.2 | 13.8 | 33.1 |
|  | $H_2O$ | 23.5 | 21.7 | 8.4 | 7.7 | 17.4 | 28.2 | 41.2 | 31.1 | 23.7 |
|  | NaCl | 3.7 | 2.3 | 1.2 | 0.76 | 4.4 | 5.7 | 8.4 | 7.2 | 5.3 |
|  | NaCl per 10% of an active ingre- | 0.64 | 0.41 | 0.16 | 0.12 | 0.65 | 1.1 | 2.1 | 1.5 | 1.4 |

| | Example | | | | | | Comparative Example | | |
|---|---|---|---|---|---|---|---|---|---|
| | 1 | 2 | 3 | 4 | 5 | 6 | 1 | 2 | 3 |
| dient | | | | | | | | | |

*EtOH = ethanol, IPA = isopropyl alcohol

What is claimed is:

1. A process for the preparation of an amphoteric surfactant comprising reacting an alkylimidazoline or an open-ring derivative thereof with a monohaloacetic acid or a salt thereof in the presence of an alkali in a water/lower alcohol mixture, characterized by carrying out the reaction by using (a) an alkylimidazoline or an open-ring derivative thereof, (b) a lower alcohol and (c) water each in such an amount that the composition by weight of the components (a), (b) and (c) is within a pentagon defined by points (80,10,10), (80,15,5), (40,55,5), (40,27.5,32.5) and (52.5,10, 37.5) in triangular coordinates wherein each of the components (a), (b) and (c) is placed at each of the three vertices of said coordinates, with the proviso that the amount of water does not include the one required for the ring opening of the alkylimidazoline, and removing precipitated inorganic salts by filtration.

2. A process for the preparation of an amphoteric surfactant as set forth in claim 1, wherein the molar ratio of the alkylimidazoline or the open-ring derivative thereof to the monohaloacetic acid or the salt thereof is between 1 : 1.0 and 1 : 3.0.

3. A process for the preparation of an amphoteric surfactant as set forth in claim 1, wherein the lower alcohol is ethanol or isopropanol.

* * * * *